(12) United States Patent
Arevalos et al.

(10) Patent No.: US 10,264,981 B2
(45) Date of Patent: Apr. 23, 2019

(54) INTRODUCER SHEATH WITH ELECTRODES

(71) Applicant: SARANAS, INC., Houston, TX (US)

(72) Inventors: Christopher Alexander Arevalos, Houston, TX (US); Mehdi Razavi, Houston, TX (US); Matthew DeNardo, Watertown, MA (US); Serge Roux, Boston, MA (US); Joe Bailey, Reading, MA (US); Arun Venkatasubramanian, Arlington, MA (US)

(73) Assignee: Saranas, Inc., Houston, TX (US)

(*) Notice: Subject to any disclaimer, the term of this patent is extended or adjusted under 35 U.S.C. 154(b) by 909 days.

(21) Appl. No.: 14/829,016

(22) Filed: Aug. 18, 2015

(65) Prior Publication Data
US 2017/0049359 A1 Feb. 23, 2017

(51) Int. Cl.
*A61B 5/053* (2006.01)
*A61B 5/02* (2006.01)
(Continued)

(52) U.S. Cl.
CPC ........ *A61B 5/02042* (2013.01); *A61B 5/0538* (2013.01); *A61B 5/6852* (2013.01); *A61M 25/0662* (2013.01); *A61M 2025/0166* (2013.01)

(58) Field of Classification Search
CPC ... A61B 5/068; A61B 5/02042; A61B 5/0538; A61B 5/6852; A61B 5/0295; A61B 5/6885; A61B 5/6886; A61B 2562/0209
See application file for complete search history.

(56) References Cited

U.S. PATENT DOCUMENTS 3,995,623 A * 12/1976 Blake ................. A61B 5/02158
600/381
5,500,012 A * 3/1996 Brucker ............... A61B 5/0422
604/22
(Continued)

FOREIGN PATENT DOCUMENTS

| WO | 2013/169667 A1 | 11/2013 |
| WO | 2015/003134 A1 | 1/2015 |
| WO | 2015/003138 A1 | 1/2015 |

OTHER PUBLICATIONS

International Patent Application No. PCT/US2016/046263 International Search Report and Written Opinion dated Nov. 16, 2016 (11 pages).

(Continued)

*Primary Examiner* — Lee S Cohen
*Assistant Examiner* — Erin M Cardinal
(74) *Attorney, Agent, or Firm* — Blank Rome LLP

(57) ABSTRACT

A introducer is disclosed that includes an introducer sheath for introducing a catheter into a blood vessel at an insertion point, a plurality of electrodes on the introducer sheath, a flush line coupled to the introducer sheath including a proximal end and a distal end. In addition, the introducer includes an impedance assessment unit coupled to the flush line between the proximal end and the distal end and electrically coupled to the electrodes. The impedance assessment unit is configured to inject a predetermined current or voltage into a first of the plurality of electrodes and measure a resulting voltage or current, respectively, from a second of the plurality of electrodes.

17 Claims, 11 Drawing Sheets

(51) Int. Cl.
*A61M 25/06* (2006.01)
*A61B 5/00* (2006.01)
*A61M 25/01* (2006.01)

(56) References Cited

U.S. PATENT DOCUMENTS

| | | |
|---|---|---|
| 6,546,270 B1 | 4/2003 | Goldin et al. |
| 8,273,023 B2 | 9/2012 | Razavi |
| 8,366,615 B2 | 2/2013 | Razavi |
| 8,961,417 B2 | 2/2015 | Razavi |
| 9,474,881 B2 * | 10/2016 | Razavi .............. A61M 25/0662 |
| 2003/0009160 A1 | 1/2003 | Carroll et al. |
| 2008/0077124 A1 | 3/2008 | Lalonde et al. |
| 2009/0018455 A1 * | 1/2009 | Chang .............. A61B 17/12136 |
| | | 600/504 |
| 2009/0254166 A1 * | 10/2009 | Chou .................... A61F 2/958 |
| | | 623/1.11 |
| 2010/0059173 A1 * | 3/2010 | Kampa ............. A61M 25/0012 |
| | | 156/244.15 |
| 2012/0065469 A1 | 3/2012 | Allyn et al. |
| 2012/0108950 A1 | 5/2012 | He et al. |
| 2012/0220848 A1 * | 8/2012 | Razavi .................. A61B 5/053 |
| | | 600/371 |
| 2013/0018248 A1 * | 1/2013 | Hurezan ............. A61B 5/0402 |
| | | 600/381 |
| 2015/0011856 A1 | 1/2015 | Arevalos |
| 2015/0012007 A1 | 1/2015 | Arevalos |

OTHER PUBLICATIONS

International Patent Application No. PCT/US2016/046263 International Preliminary Report on Patentability dated Feb. 20, 2018 (8 pages).

European Patent Application No. 16837518 Supplementary European Search Report dated Nov. 20, 2018 (8 pages).

* cited by examiner

INTRODUCER SHEATH WITH ELECTRODES

CROSS-REFERENCE TO RELATED APPLICATIONS

This disclosure contains subject matter that may be related to subject matter contained in U.S. Pat. Nos. 8,273,023, 8,961,417, 8,366,615, U.S. Patent Application Publication No. 2012/0220848, U.S. Patent Application Publication No. 2015/0011856, U.S. Patent Publication No. 2015/0012007, International Patent Application Publication No. WO 2013/169667, International Patent Application Publication No. WO 2015/003138, and International Patent Application Publication No. WO 2015/003134, and the contents of each of these references is incorporated herein by reference in their entirety for all purposes.

STATEMENT REGARDING FEDERALLY SPONSORED RESEARCH OR DEVELOPMENT

Not applicable.

BACKGROUND

This disclosure relates generally to the field of medical devices. More specifically, the disclosure relates to a method and device using impedance for the detection of fluid (e.g., blood) bleeding such as pericardial effusion, retroperitoneal effusion, etc.

Radiofrequency ablation (RF ablation) or other invasive cardiac procedures which involve operation within the cardiac chambers, coronary arteries or the heart's venous anatomy have saved many lives. These procedures often involve percutaneous access into the cardiac chambers or epicardial arterial or venous vessels. Catheter, pacing lead, sheath, or other types of device manipulations frequently are performed as key parts of these procedures. Examples of this include balloon angioplasty or stent placement. Often, catheter access to the femoral artery is needed to enable access to the heart or elsewhere in the body.

A rare but potentially dangerous complication of these and similar procedures is inadvertent perforation of the blood vessel into which the catheter is inserted. For example, the initial needle penetration into the blood vessel may inadvertently penetrate the backside of the blood vessel, not just the front side into which an introducer sheath and catheter are to be inserted. It is not unusual in clinical procedures for the occurrence of perforation to be heralded by the onset of hemodynamic derangements such as a drop in blood pressure. In such cases the existence of the backside blood vessel perforation may not be recognized by the medical staff until a drop in blood pressure is detected. Of critical clinical significance is that early detection of such perforation may allow the operator to implement interventions (for example discontinuation of peri-operative anticoagulation) that would mitigate the untoward consequences of pericardial effusion.

Hematomas, caused by the accumulation of blood outside the blood vessel resulting from the backside perforation during catheter insertion, may cause pain, blood loss, shock, or even death. Its detection unfortunately is often not noticed right away and frequently only noted after hypotension or other symptoms are noted.

BRIEF SUMMARY

Some embodiments are directed to an introducer. In an embodiment, the introducer includes an introducer sheath for introducing a catheter into a blood vessel at an insertion point. In addition, the introducer includes a plurality of electrodes on the introducer sheath. Further, the introducer includes a flush line coupled to the introducer sheath including a proximal end and a distal end. Still further, the introducer includes an impedance assessment unit coupled to the flush line between the proximal end and the distal end and electrically coupled to the electrodes. The impedance assessment unit is configured to inject a predetermined current or voltage into a first of the plurality of electrodes and measure a resulting voltage or current, respectively, from a second of the plurality of electrodes.

Other embodiments are directed to an impedance assessment unit configured to be disposed on an introducer for inserting a catheter into a blood vessel at an insertion point. In an embodiment, the impedance assessment unit includes a body defining a cavity, a first port extending into the cavity, and a second port extending into the cavity. In addition, the impedance assessment unit includes electronic components disposed within the cavity. The electronic components are configured to inject a known current or voltage into a first of a plurality of electrodes coupled to an introducer sheath of the introducer and measure a resulting voltage or current, respectively, from a second of the plurality of electrodes. Further, the impedance assessment unit includes a power source disposed within the cavity. The cavity, the first port, and the second port are configured to receive a flush line of the introducer therethrough. The electronic components and the power source are arranged within the cavity such that when the flush line is received through the first port, the second port, and the cavity, the flush line includes a bent region extending around the power source. The bent region is configured to resist movement of the impedance assessment unit along the flush line.

Still other embodiments are directed to an introducer. In an embodiment, the introducer includes an introducer sheath for introducing a catheter into a blood vessel at an insertion point, a plurality of electrodes on the introducer sheath, and a hub coupled to the introducer sheath. In addition, the introducer includes a flush line further including a proximal end coupled to the hub, a distal end, a radially outermost surface extending between the proximal end and the distal end, and a throughbore also extending between the proximal end and the distal end. Further, the introducer includes an impedance assessment unit coupled to the flush line between the proximal end and the distal end. The impedance assessment unit includes a body defining a cavity, a first port extending into the cavity, and a second port extending into the cavity. The impedance assessment unit is coupled to the flush line such that the flush line extends through the cavity between the first port and the second port. Still further, the introducer includes a plurality of conductors extending along the flush line, between the radially outer surface and the throughbore, and coupled to the impedance assessment unit. At least one of the plurality of conductors is also coupled to a first of the plurality of electrodes and at least another one of the plurality of conductors is also coupled to a second of the plurality of electrodes. The impedance assessment unit is configured to inject a known current or voltage into the first electrode and measure a resulting voltage or current, respectively, from the second electrode.

Embodiments described herein comprise a combination of features and advantages intended to address various shortcomings associated with certain prior devices, systems, and methods. The foregoing has outlined rather broadly the features and technical advantages of the disclosed embodiments in order that the detailed description of the invention that follows may be better understood. The various characteristics described above, as well as other features, will be readily apparent to those skilled in the art upon reading the following detailed description, and by referring to the accompanying drawings. It should be appreciated by those skilled in the art that the conception and the specific embodiments disclosed may be readily utilized as a basis for modifying or designing other structures for carrying out the same purposes thereof. It should also be realized by those skilled in the art that such equivalent constructions do not depart from the spirit and scope of the disclosure.

BRIEF DESCRIPTION OF THE DRAWINGS

For a detailed description of the disclosed embodiments, reference will now be made to the accompanying drawings in which.

DETAILED DESCRIPTION OF EXEMPLARY EMBODIMENTS

Figure 1:
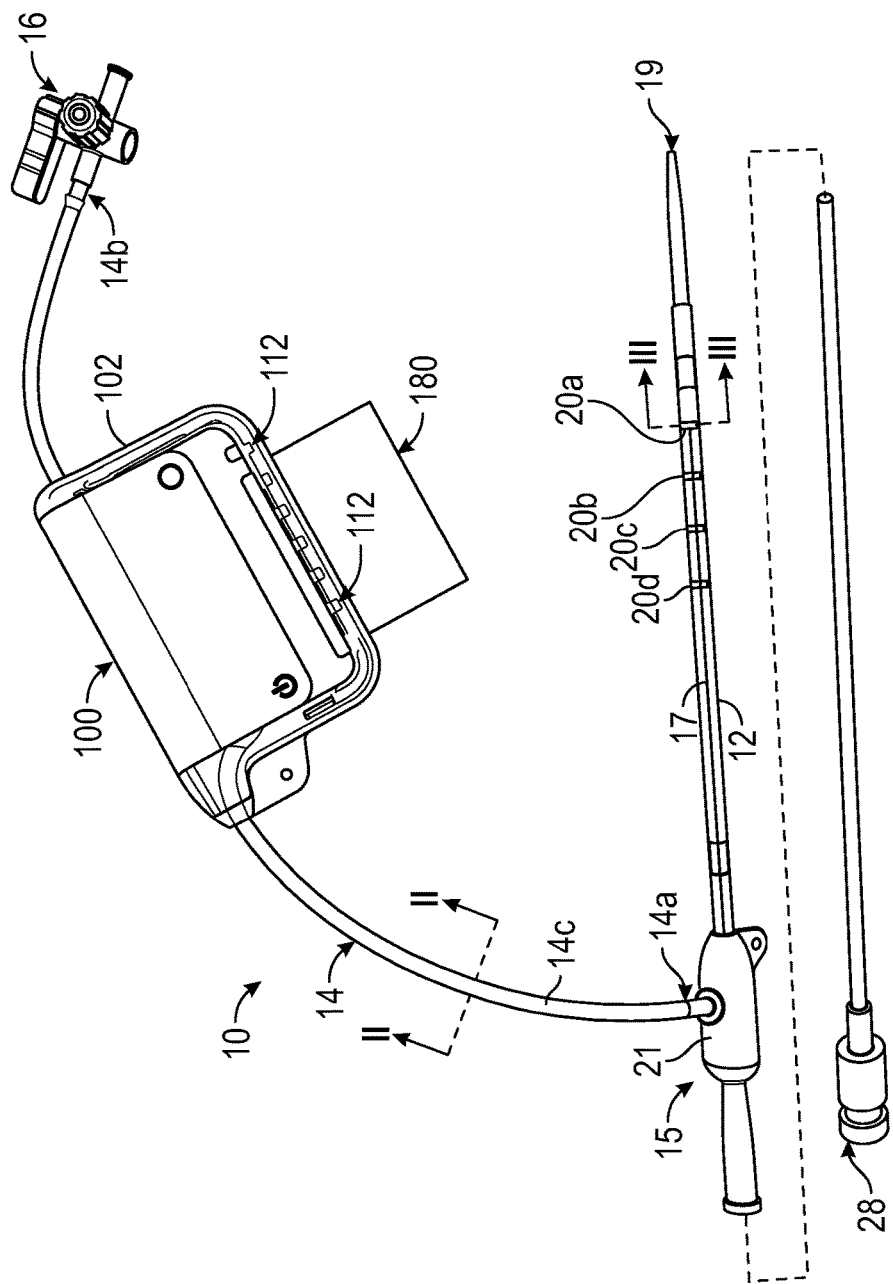
FIG. 1 is a perspective view of an introducer sheath with electrodes usable to determine impedance for the detection of bleeding in accordance with the principles disclosed herein.

The following discussion is directed to various exemplary embodiments. However, one skilled in the art will understand that the examples disclosed herein have broad application, and that the discussion of any embodiment is meant only to be exemplary of that embodiment, and not intended to suggest that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis. Further, in the following discussion and in the claims, the term "fluid" is defined to include blood and other types of body fluids or gases that may bleed or leak from a vessel or organ. All references to an impedance measurement being made encompasses any of the variations described herein as performed by the combination of the impedance assessment unit and an external apparatus.

As previously described, inadvertent perforation of a blood vessel while inserting a catheter therein is difficult to recognize quickly and can lead to dangerous complications during a medical procedure (e.g., RF ablation). As a result, it follows that a method and device which could more rapidly detect the presence of pericardial or retroperitoneal bleeding, aretrivenous fistula, or hematoma, prior to the onset of symptoms, is highly desirable. Rapid detection of such bleeding or fluid accumulation can lead to more timely management—such as aborting the procedure or reversal of the patient's anticoagulation response during such cardiac procedures. Thus, in accordance with preferred embodiments disclosed herein, a system and method are disclosed herein that involves real-time assessment of resistance or impedance of body tissue to detect a bleed condition. Accumulation of sufficient fluid or blood in areas around the blood vessel at the site of catheter insertion leads to changes in either or both of the direct current (DC) resistance and/or the complex impedance of such body tissues. A change in either the resistance or the complex impedance provides an indication that fluid has accumulated in the space around the blood vessel through which the electrical current travels. Embodiments of the invention also use conduction time between two vectors as another variable which may be analyzed. Various embodiments are described herein for measuring impedance to detect fluid bleeding. Impedance may be computed by injecting a known current (DC or AC) and measuring the resulting voltage, or imposing a known voltage across the electrodes and measuring the resulting current. The ratio of voltage to current determines impedance. Impedance can then be used to detect whether the patient is bleeding.

In accordance with one such embodiment, FIG. 1 illustrates an introducer 10 usable to insert a catheter (not shown) into a blood vessel (vein or artery). The introducer 10 comprises a hollow sheath 12 (also called an "introducer sheath") having a distal end 19 that is insertable into a blood vessel of a person. The blood vessel may be an artery or a vein. In at least one application, the blood vessel is the femoral artery, but other blood vessels may be used as well. In the illustrative embodiment of FIG. 1, one or more electrodes 20a, 20b, 20c, and 20d are provided on the sheath 12. Such electrodes can be provided at any of a variety of locations along the sheath 12. Although four electrodes are shown on sheath 12 in the example of FIG. 1, any number (one or more) can be included in other embodiments. As will be explained below, the electrodes 20a, 20b, 20c, 20d are usable to measure impedance of the person so as to detect bleeding (e.g., retroperitoneal bleeding). At least one of the electrodes used to measure impedance may be located apart from the sheath (e.g., a patch electrode adhered to the patient's skin).

Impedance between pairs of electrodes within and/or on the sheath 12 (e.g., electrodes 20a, 20b, 20c, 20d) can also be measured to assess the presence of such phenomenona as an accumulation of blood or near the sheath 12. In various embodiments, the system may use only one pair of electrodes such that the injected current and the detected voltage are from one pair of electrodes. In other embodiments, the system may use multiple pairs of electrodes such that the injected current uses one pair of electrodes and the detected voltage is from a separate pair of electrodes. For example, one pair of electrodes is used to inject current, and another pair of electrodes is used to measure the resulting voltage to thereby assess impedance, or vice versa (a known voltage is imposed on pair of electrodes and current is measured). Although two different pairs of electrodes are used, an electrode may be common to both pairs. Other configurations utilizing multiple electrodes are also feasible embodiments.

Figure 2:
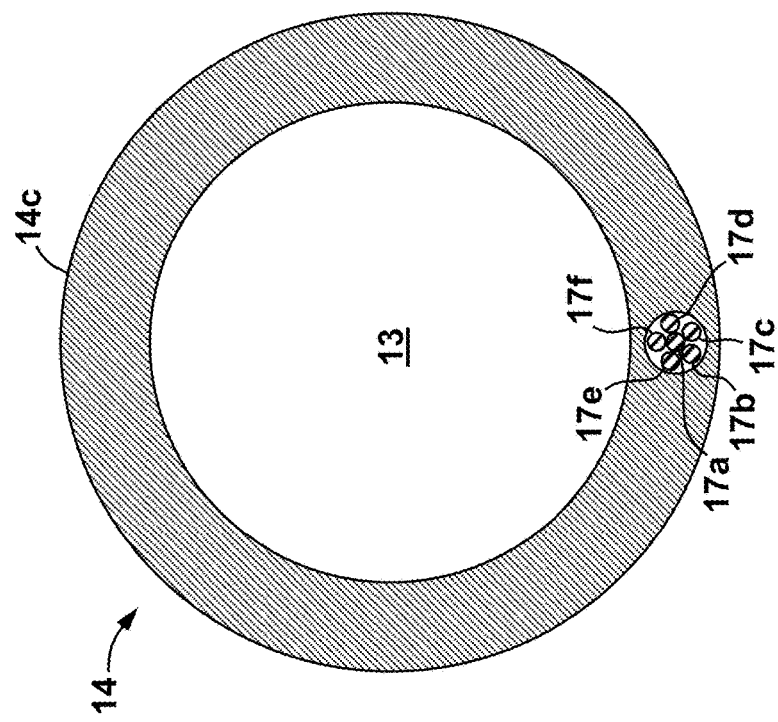
FIG. 2 is a cross-sectional view of the flush line of the introducer of FIG. 1 taken along section II-II.

The sheath 12 may be coupled to a hub 15 which may incorporate a hemostasis valve 21 from which a side arm or flush line 14 may extend that allows the sheath 12 to be used to administer fluids and or drugs. Flush line 14 includes a first or proximal end 14a coupled to hub 15 and a second or distal end 14b opposite proximal end 14a, an outer surface 14c extending between ends 14a, 14b, and as is best shown in FIG. 2, a central throughbore 13 also extending between ends 14a, 14b. A valve 16 is coupled to the distal end 14b, and is configured to allow, restrict, and/or adjust fluid communication along throughbore 13 during operations. The introducer 10 also includes a dilator 28 that is insertable into the hollow sheath 12. The dilator 28 and sheath 12 function to permit a catheter (not shown) to be inserted into the blood vessel. Independently from the preceding features, the sheath 12 may also include other features to facilitate simple "peel-away" removal without disturbing a catheter having been passed the lumen of the sheath 12.

Referring still to FIG. 1, electrical conductors 17 (e.g., wires) extend along at least part of the sheath 12 from the electrodes 20a, 20b, 20c, 20d to hub 15, where they are then routed within (or on the inside or outside of) the wall of flush line 14 to an impedance assessment unit 100 which is coupled to flush line 14 between ends 14a, 14b. The specific construction and function of impedance assessment unit 100 will be described in more detail below. Referring briefly to FIG. 2, conductors 17 routed along flush line 14 between throughbore 13 and outer surface 14c. The conductors 17 preferably include at least one insulated conductor for each electrode (e.g., electrodes 20a, 20b, 20c, 20d). In this embodiment conductors 17 comprise a total of six (6) conductors 17a, 17b, 17c, 17d, 17e, 17f, where the conductors 17a, 17b, 17c, 17d are coupled to electrodes 20a, 20b, 20c, 20d, respectively, and conductors 17e and 17f couple the impedance assessment unit 100 to an automatic switch assembly contained, for example, in the hub 15 and which will be described in more detail below. The conductors 17a, 17b, 17c, 17d are usable to conduct signals between electrodes 20a, 20b, 20c, 20d on the sheath 12 and the impedance assessment unit 100 disposed on flush line 14. Impedances between any individual pair electrodes may be measured. It also should be appreciated that in other embodiments, conductors 17 are routed either inside or within sheath 12 (e.g., in a similar manner described above for flush line 14).

Figure 3:
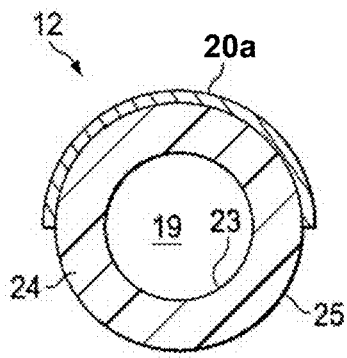
FIGS. 3-6 are cross-sectional views of the sheath of the introducer of FIG. 1 taken along section III-III and showing various positions for the electrodes along and within the sheath.
Figure 4:
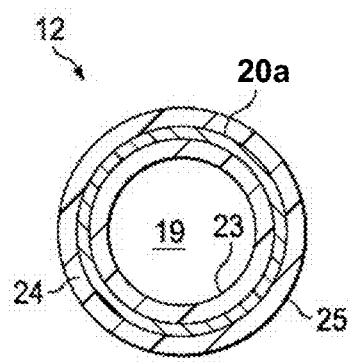
Figure 5:
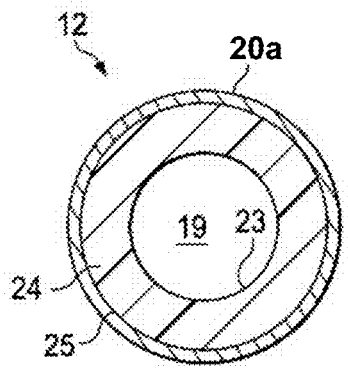

FIGS. 3-6 illustrate various embodiments of the electrodes 20a; however it should be appreciated that each of the other electrodes 20b, 20c, 20d may be similarly situated along sheath 12. Each Figure (i.e., FIGS. 3-6) shows a cross-sectional view of the sheath 12 facing distal end 19 along section III-III in FIG. 1. Referring first to FIG. 3, sheath 12 comprises material 24 formed as a tubular member and comprising an inner surface 23 and an outer surface 25. In the embodiment of FIG. 3, the electrode 20a comprises a partial ring electrode disposed about a portion of the perimeter of the outer surface 25. In some embodiments, the electrode 20a is adhered (e.g. via glue) to the outer surface 25. In other embodiments, the electrode 20a covers more than 50% of the perimeter of the outer surface 25 and is retained (e.g., clamped) in place like a bracelet. FIG. 5 illustrates an embodiment of the electrode 20a in which the electrode 20a is a complete ring electrode (i.e., completely surrounds the outer surface 25 of the sheath 12).

Figure 6:
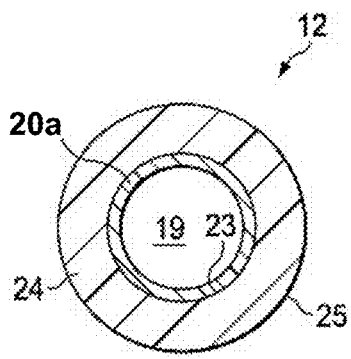

In FIGS. 3 and 5, the electrode 20a is provided on the outer surface 25 of the sheath. In contrast, in the embodiment of FIG. 4, the electrode 20a is embedded within the material 24 of the sheath 12 in which case the sheath materials (or at least the segments of the sheath material between the electrodes) must be conductive of electrical signals in the range employed. Furthermore, for the purposes of detection of clot, impedance or conduction (for detecting bleeding) between these electrodes may be measured. In FIG. 6, the electrode 20a is provided on the inner surface 23 of the sheath 12 and thus within the inner hollow portion of the sheath.

In some embodiments, the electrode 20a is located on the sheath 12 so that the electrode 20a will be inside the blood vessel once the sheath 12 is inserted into the vessel. In other embodiments, the electrode 20a (or at least one of the electrodes 20a, 20b, 20c, 20d) may be provided on the sheath 12 at the proximal end outside the blood vessel (and perhaps even outside the person's body). In such embodiments, the electrode 20a (or any of the electrodes 20a, 20b, 20c, 20d) preferably is provided on the inner surface of the sheath (similar to that shown in FIG. 5). Normally, the sheath 12 is filled with body fluid (e.g., blood).

Figure 7:
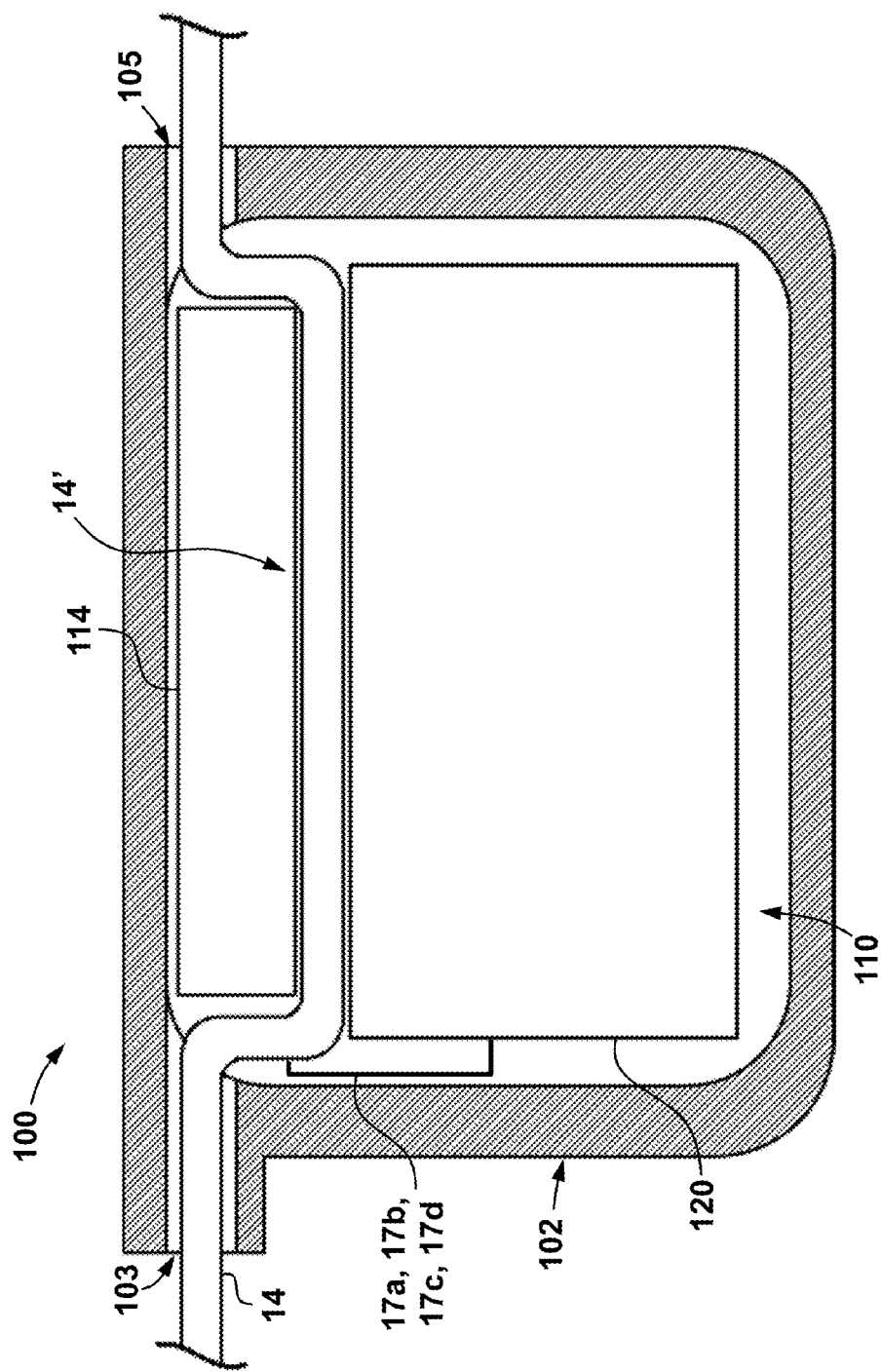
FIG. 7 is a top cross-sectional view of the impedance assessment unit of the introducer of FIG. 1.
Figure 8:
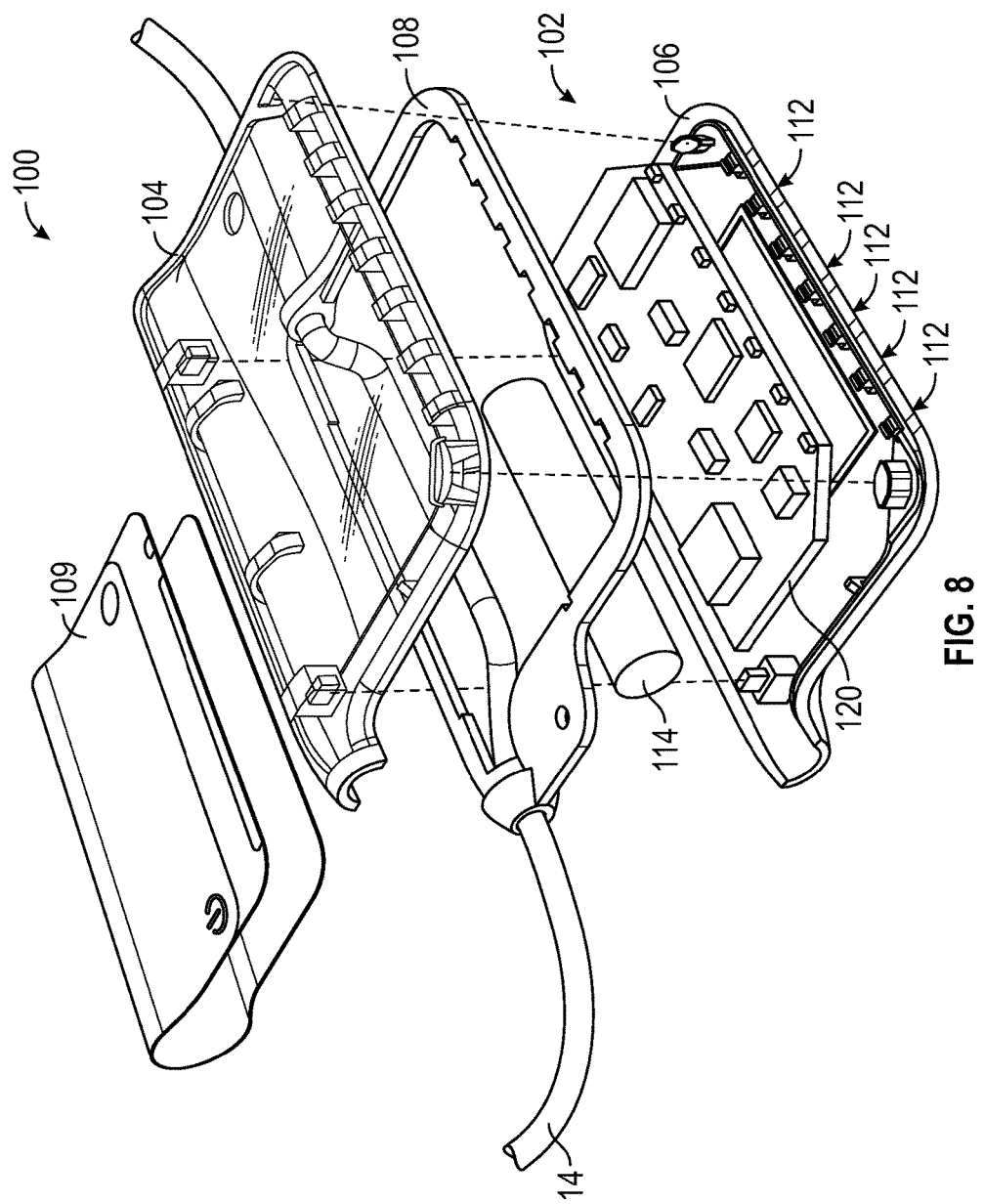
FIG. 8 is an exploded view of the impedance assessment unit of the introducer of FIG. 1.

Referring now to FIGS. 1, 7, and 8, impedance assessment unit 100 connects to electrodes 20a, 20b, 20c, 20d via conductors 17a, 17b, 17c, 17d, respectively, and is used during impedance measurement operations. In this embodiment, unit 100 includes an outer shell or body 102 that defines an inner cavity 110. As is best shown in FIGS. 7 and 8, cavity 110 houses a power source 114 and various other electronic components (shown collectively at reference numeral 120). In some embodiments power source 114 is a battery (disposable or rechargeable); however, any suitable source of electric power may be utilized while still complying with the principles described herein. For example, in other embodiments power source 114 may comprise a charged capacitor, a wireless power receiver, or combinations thereof.

Body 102 includes a first port 103 and a second port 105 each extending into cavity 110. As will be described in more detail below, flush line 14 is routed through cavity 110 of unit 100 via ports 103, 105 during assembly of introducer 10. As is schematically shown in FIG. 7, conductors 17a, 17b, 17c, 17d emerge from flush line 14 within cavity 110 and route to the electronic components 120 disposed therein thereby ensuring connection (e.g., electrical connection)

between electrodes 20a, 20b, 20c, 20d and the components within cavity 110 during operations. As is best shown in FIG. 8, body 102 comprises a first or upper housing member 104, a second or lower housing member 106, and a gasket or sealing member 108 disposed between housing members 104, 106. Together, housing members 104, 106, and gasket 108 define cavity 110 and ports 103, 105. An outer covering member 109 is disposed about each of the housing members 104, 106 to provide appropriate labeling and covering for various components of unit 100. In this embodiment, a plurality of indicator lights 112 are disposed along an edge of body 102. Lights 112 are utilized to provide feedback to a user (e.g., a physician, technician, etc.) to facilitate and optimize operations with unit 100 and introducer 10. In this embodiment, lights 112 are light emitting diodes (LED); however, it should be appreciated that any suitable light emitting device may be used while still complying with the principles disclosed herein.

Referring to FIGS. 7 and 8, when impedance assessment unit 100 is clamped to or otherwise connected to flush line 14 of introducer 10, flush line 14 is routed through cavity 110 through ports 103, 105 as previously described. Specifically, as is best shown in FIG. 7, flush line 14 extends through cavity 110 between ports 103, 104 and is routed between power source 114 and the other various electronic components 120 disposed within cavity 110. In other words, in the embodiment of FIG. 7, flush line 14 is sandwiched between power source 114 and electronic components 120 within cavity 110. In this embodiment, because power source is aligned between ports 103, 105, flush line 13 is curved or bent around power source 14 as it extends between ports 103, 105 as shown. Without being limited to this or any other theory, this curved or bent region 14' in flush line 14 provides resistance to the free movement of impedance assessment unit 100 along flush line 14 during operations. In particular, sliding engagement of body 102, particularly ports 103, 105, along line 14 is resisted due to engagement of outer surface 14c (FIG. 2) of the flush line and inner surfaces of body 102 proximate ports 103, 105. Again, without being limited to this or any other theory, such resistance to the free movement of unit 100 along flush line 14 prevents over tensioning of conductors 17a, 17b, 17c, 17d, which could lead to a loss of connectivity between conductors 17a, 17b, 17c, 17d and electrodes 20a, 20b, 20c, 20d, respectively, and/or electronic components 120 of unit 100 as a result of, for example, breakage of one or more of the conductors 17a, 17b, 17c, 17d.

Figure 9:
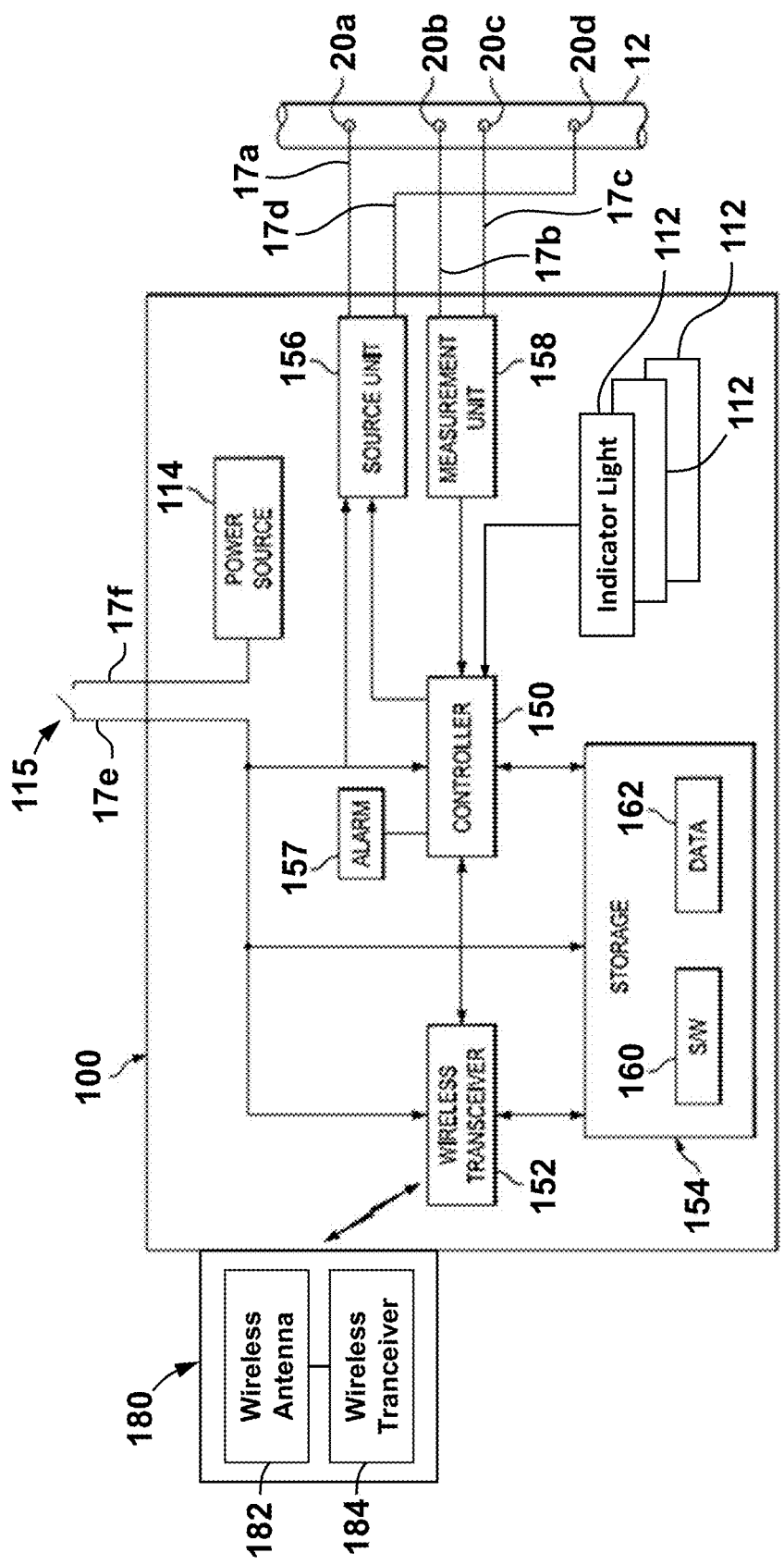
FIG. 9 is a block diagram of the impedance assessment unit of the introducer of FIG. 1.

FIG. 9 shows a block diagram of the impedance assessment unit 100. As previously described, cavity 110 within impedance assessment unit 100 houses power source 114 and various electronic components (e.g., components collectively shown in FIG. 7 at reference numeral 120) such as those shown in the example of FIG. 9. As shown in the example of FIG. 9, the electronic components include a controller 150, a wireless transceiver 152, storage 154, a source unit 156, an alarm 157, indicator lights 112, and a measurement unit 158. The power source 114 provides electrical power to the electronic components such as the controller 150, wireless transceiver 152, storage 154, and source unit 156.

The controller 150 executes software 160 provided on storage 154. The controller 150, upon executing software 160, provides the impedance assessment unit 100 with some or all of the functionality described herein. The storage 154 may comprise volatile storage (e.g., random access memory), non-volatile storage (e.g., flash storage, read only memory, etc.), or combinations of both volatile and non-volatile storage. Data 162 consumed or produced by the software can also be stored on storage 154. For example, measured current or voltage values, computed impedance values, bleed detection alerts, etc. can be stored on storage 154 pending wireless transmission through the wireless transceiver 152 to an external apparatus (e.g., a bedside monitor, computer, etc.).

The wireless transceiver 152 may be implemented in accordance with any suitable wireless protocol such as near field communication (NFC), BLUETOOTH®, WiFi (any of the IEEE 802.11x family of protocols), etc. The transceiver 152 may be capable of transmitting only, or may be capable of transmitting and receiving. The controller 150 causes the wireless transceiver to transmit values indicative of impedance (current, voltage) or impedance values themselves. The transceiver 152 may be a bi-directional device to permit outgoing transmissions of data, as well as receive incoming commands from an external apparatus. For example, an external apparatus may send a command to the controller 150 via the wireless transceiver 152 to command the impedance assessment unit 100 to initiate a process by which impedance is determined, or to transmit previously stored data (e.g., current, voltage, and/or impedance).

In some embodiments, wireless transceiver 152 is a NFC unit that is configured to communicate wirelessly with components that are relatively close (within 3.9 in or 10 cm or less) to the wireless transceiver. Thus, in such embodiments, as is shown in both FIGS. 1 and 9, impedance assessment unit 100 can be wirelessly coupled to a wireless communication unit 180 which includes a wireless transceiver 182 and a wireless antenna 184. The wireless communication unit 180 preferably is external to the impedance assessment unit 100, and may be releasably connected to body 102 of unit 100 during operations to establish communications between unit 100 and other components and/or devices which are disposed relatively far from unit 100 (e.g., a bedside monitor, computer, etc.). Specifically, wireless transceiver 184 is configured to receive NFC communications emitted from transceiver 152 when wireless communication unit 180 is brought close enough to assessment unit 100 for NFC communications. The signals and/or the data encoded in the signals received by transceiver 184 from the impedance assessment unit 100 then can be wirelessly forwarded to another external apparatus (e.g., separate computing device and/or a bedside monitor) by antenna 182. The wireless protocol used by the wireless communication unit 180 to communicate with an external apparatus such as a bedside monitor may be a longer range protocol than NFC. For example, the communication protocol between wireless communication unit 180 and the bedside monitor may be WiFi, BLUETOOTH®, etc.

Wireless communication unit 180 may be coupled or connected to any portion of body 102 of impedance assessment unit 100 through any suitable connection method while still complying with the principles disclosed herein. For example, communication unit 180 may be connected to body 102 of impedance assessment unit 100 with one or more snaps, magnets, brackets, mechanical connectors (e.g., pin like connectors), etc. In at least some embodiments, the communication unit 180 is releasably connected to body 102 of impedance assessment unit 100 in order to allow for quick detachment of unit 180 from unit 100 during operations. Specifically, in at least some embodiments, impedance assessment unit 100 is designed as a single use device, which is discarded after the initial use. Thus, providing for a readily releasable connection between impedance assessment unit 100 and communication unit 180 allows a user to utilize communication unit 180, which may include more robust and/or expensive electronic components, with multiple different impedance assessment units 100 over the operating life of a single unit 180.

The source unit 156 receives power from the power source 114 and generates a current or voltage under control by the controller 150. The source unit 156 may generate a predetermined current or voltage, and is broadly referred to as a source unit to indicate either or both possibilities. The source unit 156 is connected to a pair of electrodes (electrodes 20a and 20d in the example of FIG. 9). As a current source, the source unit 156 injects a predetermined (i.e., fixed) current through one of the electrodes 20a, 20d and receives the return current through the other of the electrodes 20a, 20d. The injected current may comprise a series of pulses or a sustained current. The amplitude of the current may be in the sub-physiological range such as 1 milliamp. If a pulse train is used, the pulse width may be 0.2 milliseconds or less and have a frequency between 5,000 and 500,000 Hz or higher. Additionally or alternatively, the source unit 156 may inject current at a plurality of frequencies simultaneously. The plurality of frequencies may, for example, by five frequencies, which may be 5 KHz, 10 KHz, 50 KHz, 100 KHz, and 500 KHz.

The measurement unit 158 measures the resulting voltage or current. That is, if the source unit 156 injects a predetermined current into the patient, the measurement unit 158 measures the resulting voltage. If the source unit 156 imposes a predetermined voltage across electrodes 20a, 20d, the measurement unit 158 measures the resulting current. In either case, the measurement unit 158 provides the measured electrical parameter to the controller 150.

The controller 150 thus knows the magnitude of the predetermined current or voltage generated by the source unit 156 and the magnitude of the measured voltage or current from the measurement unit 158. As such, the controller 150 can compute impedance as the ratio of voltage to current and transmit the computed impedance to the external apparatus. However, as noted above, the controller 150 may not compute impedance and instead may transmit the measured electrical parameter (voltage or current) to the external apparatus for the external apparatus to compute impedance. The external apparatus may or may not know what predetermined current or voltage was set by the source unit 156. If the external apparatus does know the magnitude of the source unit's current/voltage, that value need not be (but of course can be) transmitted to the external apparatus. If the external apparatus is not aware of the source unit's current/voltage magnitude, the controller 150 preferably transmits both the measured voltage/current from the measurement unit 158 and the source unit's predetermined current/voltage.

In addition, as will be described in more detail below, controller 150 and/or the external apparatus may be utilized to detect a bleed based on the impedance measurements. Thus, in some embodiments, controller 150 may calculate impedance and then detect a bleed as a result. In other embodiments, controller 150 may calculate impedance and may then transmit the calculate impedance values to the external apparatus (e.g., bedside monitor) which then performs bleed detection operations. In still other embodiments, controller 150 transmits the measured electrical parameter (voltage or current) to the external apparatus, so that the external apparatus can then compute the impedance and perform bleed detection operations.

The example of FIG. 9 also includes a power switch 115 which, when closed turns the impedance assessment unit 100 on. In some embodiments, power switch 115 may be provided in hub 15. Insertion of the catheter or dilator 28 into the sheath 12 mechanically causes the switch 115 to close thereby activating the impedance assessment unit 100. In other embodiments, power switch 115 is provided on the outer covering member 109 and is activated by a user during operations (e.g., by pressing a button). As shown in FIG. 9, switch 115 is electrically coupled to power source 114 and the other components of impedance assessment unit 100 (e.g., controller 150, transceiver 152, storage 154, source unit 156, measurement unit 158, etc.) through conductors 17e, 17f.

Figure 10:
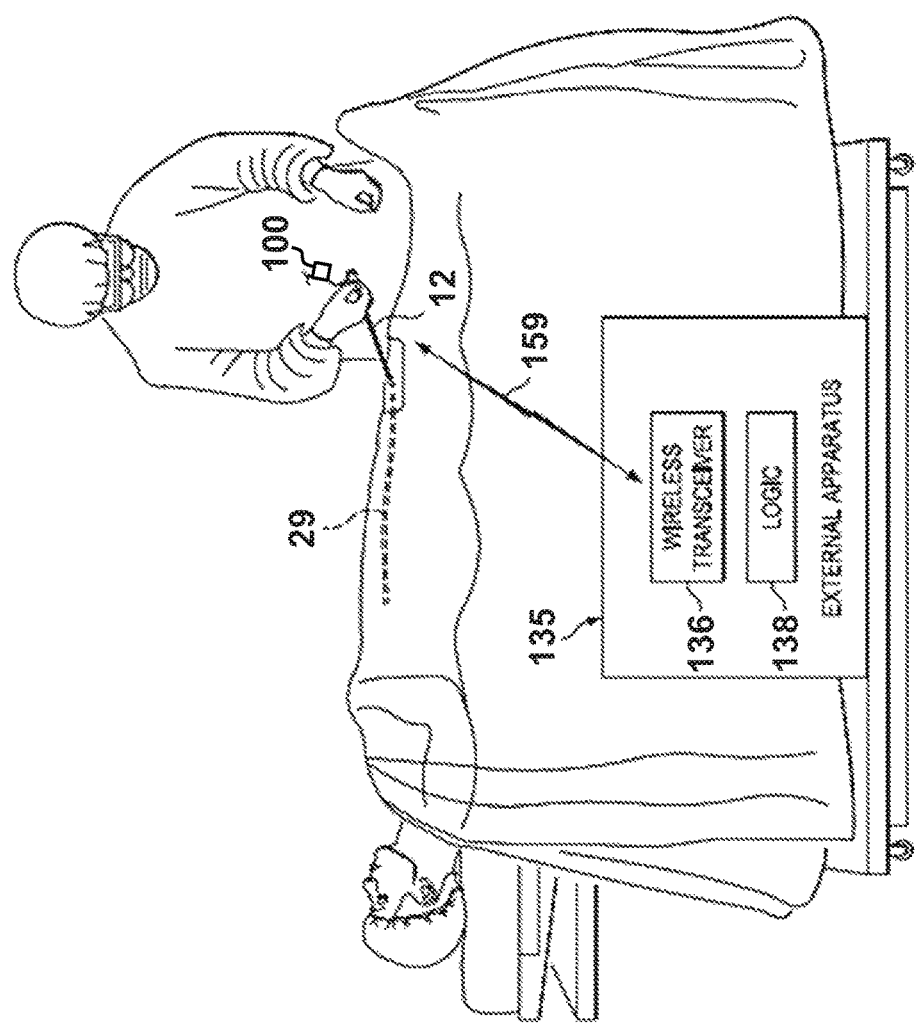
FIG. 10 shows a schematic view of the use of the impedance assessment unit and introducer of FIG. 1.

FIG. 10 illustrates an application of the use of the impedance assessment unit 100. Sheath 12 coupled to impedance assessment unit 100 is inserted into a patient's blood vessel 29 as shown and a wireless communication link 159 is established to an external apparatus 135 (via antenna 182). The wireless communication link 159 may be between the external apparatus 135 and the wireless communication unit 180 attached to the impedance assessment unit 100. The external apparatus 135 may contain a corresponding wireless transceiver 136 as well as logic 138. The external apparatus may be a computer (desktop, laptop, notebook, etc.), a smart phone, or any other type of device capable wirelessly interacting with the impedance assessment unit 100 of sheath 12. In some embodiments, the external apparatus 135 is, or is built into, a bedside monitor.

The external apparatus 135 may also comprise a means of receiving inputs from a user (not shown) so that user may configured the impedance assessment unit 100 to perform monitoring of events at predetermined times or, alternatively to set a desired time frame, i.e., every 5 seconds, for the controller 150 to perform an impedance assessment and bleed detection as described in more detail below. For example, the input may be a knob used to select one of several periods (e.g., 1 second, 5 seconds, 10 seconds, 1 minute, etc.) or the input device may be a computer drop down menu with the same time frames. Alternatively, the external apparatus 135 may contain a manual trigger so that the analysis is performed whenever the trigger is activated. Further, the input device may allow a user to enter a specific time for performing the analysis (e.g., every 10 minutes).

Regardless of whether the impedance assessment unit 100 computes impedance or transmits the necessary data for the external apparatus 135 to compute the impedance, the computed impedance may be resistance based on DC current/voltage. In other embodiments, AC current/voltage is used and complex impedance is computed as a magnitude and a phase. AC currents/voltages have an associated frequency and impedance measurements can be made at any one or more of multiple different frequencies. All references to an impedance measurement being made encompass any of the variations described herein as performed by the combination of the impedance assessment unit and an external apparatus.

Impedance measurements made at certain frequencies may provide more useful information than at other frequencies. At certain frequencies, it may be difficult to detect a bleed, where as other frequencies, bleed detection is easier. Further, the particular frequenc(ies) useful to detect a bleed may vary from patient to patient. Accordingly, a calibration is performed at the beginning of a procedure using a sheath as described in more detail below. The calibration may entail performing multiple impedance measurements at various frequencies. In some implementations, the range of acceptable frequencies is from 1000 Hz to 200 KHz, although a different frequency range may be acceptable as well. Within the frequency range, multiple discrete frequencies are chosen to make the impedance measurement. For example, 10 KHz may be chosen as well as 1000 Hz, and 100 KHz.

The source unit 156 within impedance assessment unit 100 may be capable of injecting an AC current (or generating an AC voltage) at various frequencies as commanded by the controller 150. The controller 150 preferably is configured (e.g., by way of software 260) to initiate multiple impedance measurements at various frequencies during the calibration process. Each measured electrical parameter (e.g., voltage) may be stored in data 162 in storage 154 and mapped to the frequency of the source signal (e.g., current) that caused the measured voltage to occur. Thus, multiple AC voltages (or current) may be stored in storage 154, one voltage (or current) corresponding to each AC current (or voltage) frequency. The measured parameters may be kept in storage 154 and/or wirelessly transmitted to the external apparatus 135.

The calibration process may be initiated in any suitable manner. For example, a wireless command to initiate the calibration process may be transmitted from the external apparatus 135 to the impedance assessment unit 100. Alternatively, impedance assessment unit 100 may have a user input control (e.g., a button, switch, etc.) that a user can activate to initiate the calibration process. Further still and in the case in which the power source is a battery, an electrically insulative strip may prevent at least one of the battery's contacts from connecting to the rest of the impedance assessment unit 100 circuitry. Removal of the strip may cause the controller 150 to initialize and start the calibration process.

Then, at predetermined time periods (e.g., once per minute) after calibration, the controller 150 initiates additional impedance measurements to be made. At the expiration of each such time period, the controller 150 may also cause multiple impedance measurements to be initiated at the same frequencies used during the calibration process. After computing the impedance values at the various frequencies (whether the impedance assessment unit 100 or the external apparatus 135 makes the computation as explained above), a comparison is made between each such impedance value and a previously computed impedance value. The previously computed impedance value may be the impedance value computed during calibration or any other previously computed impedance values. A determination is made as to whether the difference, as an absolute value, between the impedance value and the previously computed impedance value (e.g., calibration impedance value) is greater than a predetermined threshold. An impedance difference greater than the threshold is an indicator of a bleed. Another way to make the comparison is to compute a ratio of the current impedance value to the previously computed impedance value and then compare the ratio to a predetermined range. A ratio being outside the range is an indicator of a bleed. Bleeds may be easier to detect at certain frequencies rather than others for certain patients and thus the probability is higher that an actual bleed will be detected if multiple frequencies are used.

The process of taking impedance measurements and comparing to a previous impedance value (e.g., calibration impedance values) is repeated at the expiration of each subsequent time period. Additionally or alternatively, the impedance assessment unit 100 may be triggered manually to initiate an impedance measurement. The user can activate the user control noted above, if such a user control is provided, or the external apparatus 135 may wirelessly transmit a command to cause the controller 150 to initiate a new impedance measurement.

Referring again to FIG. 9, in embodiments in which the impedance assessment unit 100 computes impedance, the controller 150 may activate the alarm 157 if a potential bleed is detected. The alarm 157 may be an audible indicator such as a piezo-electric device. In addition, in at least some embodiments, the controller 150 may additionally or alternatively activate one or more of the indicator lights 112 upon detecting a potential bleed.

Figure 11:
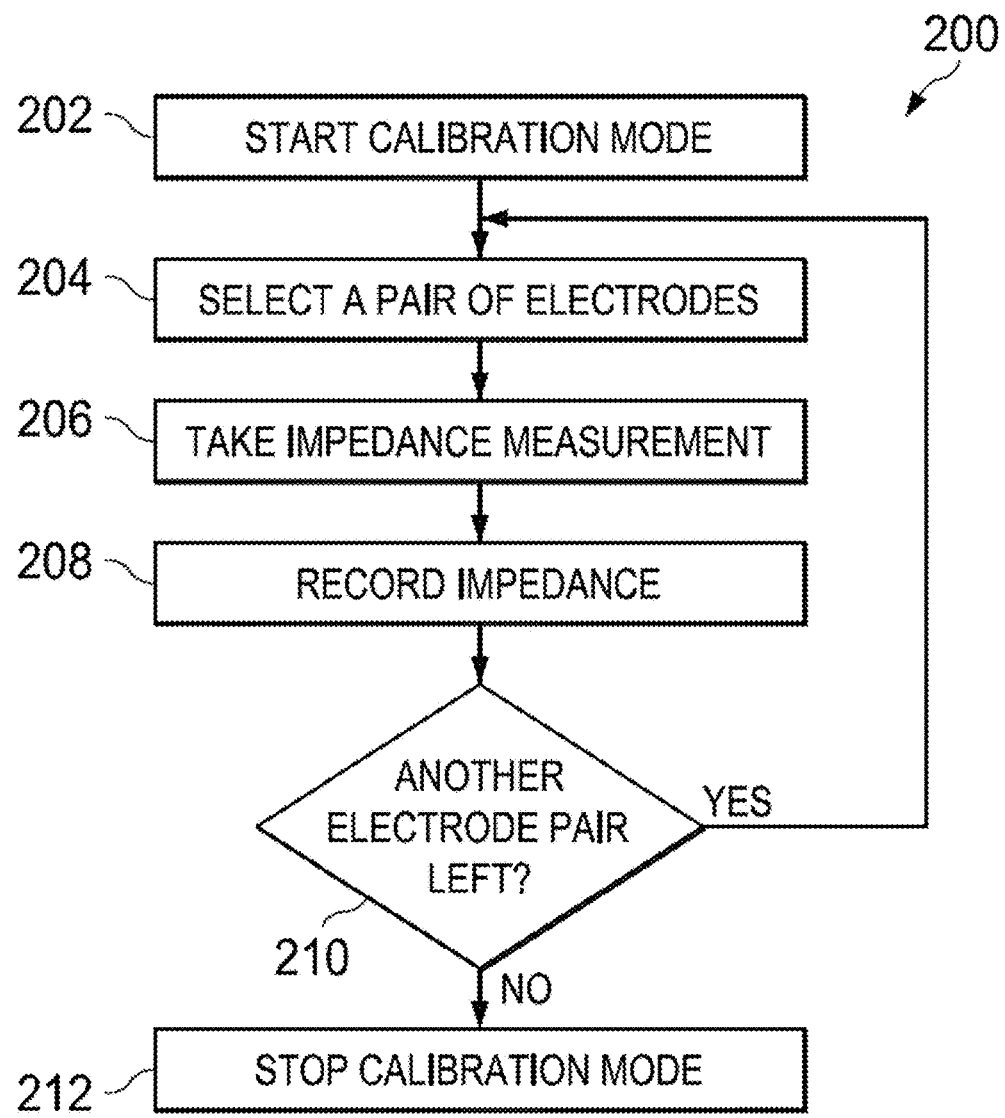
FIGS. 11 and 12 are block diagrams of methods in accordance with various embodiments.

FIG. 11 illustrates a method 200 for calibrating the impedance measuring apparatus (135 or 150) for detecting a bleed in a patient (e.g., internal bleeding). In some embodiments, the impedance assessment unit 100 and/or the external apparatus 135 comprises a calibration mode that can be initiated by a user of the impedance measuring apparatus (e.g., by pressing a button). In this embodiment, the controller 150 of the impedance assessment unit 100 executes calibration software (external apparatus 135 may also have similar software to be executed by a processor) that may be stored within storage 154. FIG. 11 is a method performed by the controller 150 (or a processor disposed within external apparatus 135) upon executing the calibration software in storage 154. The calibration mode is performed preferably before the medical procedure [e.g., coronary angiography (after the wire has been placed through the blockage but before angioplasty) or electrophysiology study (after catheters have been placed in the coronary sinus but before delivery of radiofrequency ablation)] begins.

The calibration mode begins at 202. A pair of electrodes (i.e., a pair of the electrodes 20a, 20b, 20c, 20d) is selected at 204 and at 206 and 208, an impedance measurement is taken and the computed impedance is recorded (e.g., stored in storage 154) (as amplitude and/or phase values). Preferably, the impedance measurement for a selected pair of electrodes is taken over the course of several breaths by the patient. The impedance computed for the selected impedance vector will vary during a respiratory cycle. By taking the impedance measurement over the course of several breaths (e.g., 10 seconds), the impedance measuring apparatus can account for the normal variations in impedance. The threshold (amplitude or phase) may be computed as an average during the recording period or may be set as the peak value detected (or a value slightly higher (e.g., 5% higher) than the peak). At 210, the impedance measuring apparatus determines whether there is an additional impedance vector for which a threshold is to be determined. If there is, control loops back to step 204 at which such an electrode pair is selected. If no more electrode pairs are to be selected at 210, than the calibration mode stops at 212. This calibration process may take several minutes. The same calibration variables may be measured for conduction velocities.

Once the calibration process is completed, the medical procedure (which might result in bleeding or clot formation) can begin. Any bleeding will be detected as a change in impedance deviating from an impedance threshold that is determined through the calibration process 200 (e.g., an increase above the threshold or decrease below the threshold).

The impedance measuring techniques described herein to detect bleeding are also usable to detect a hemothorax. In this application, additional, non-sheath electrode locations would include the anterior chest and posterior chest walls, the esophagus at the level near the heart, the trachea, as well as numerous intravascular and intra-cardiac and intra-coronary locations. The electrodes may be on catheters or wires.

With regards to conduction velocity, the logic (e.g., that contained in the measuring devices described herein)

assesses the conduction time between the onset of the electrical impulse in the first (transmitting) electrode and second (receiving) electrode. These electrodes are identical to the electrodes described in embodiments of this invention. The electrical output is in the same range with regards to frequency and amplitude. The measured variable, however, is the difference (delta) in time (usually milliseconds) between onset of stimulus (electrical output) in the transmitting electrode and sensing of that impulse (electrical sensing) in the receiving electrode. Conduction velocity is heterogeneous with variations in tissue characteristic. As fluid develops, the conduction velocity between the transmitting and receiving electrode will also change. This will be noted as a deviation from a baseline values (similar to the impedance values/thresholds described herein). An alert will then be issued. The various embodiments of apparatus and methods described above can also be used to measure conduction velocity and use conduction velocity to determine thickening of the heart and the presence of fluid bleeding.

Figure 12:
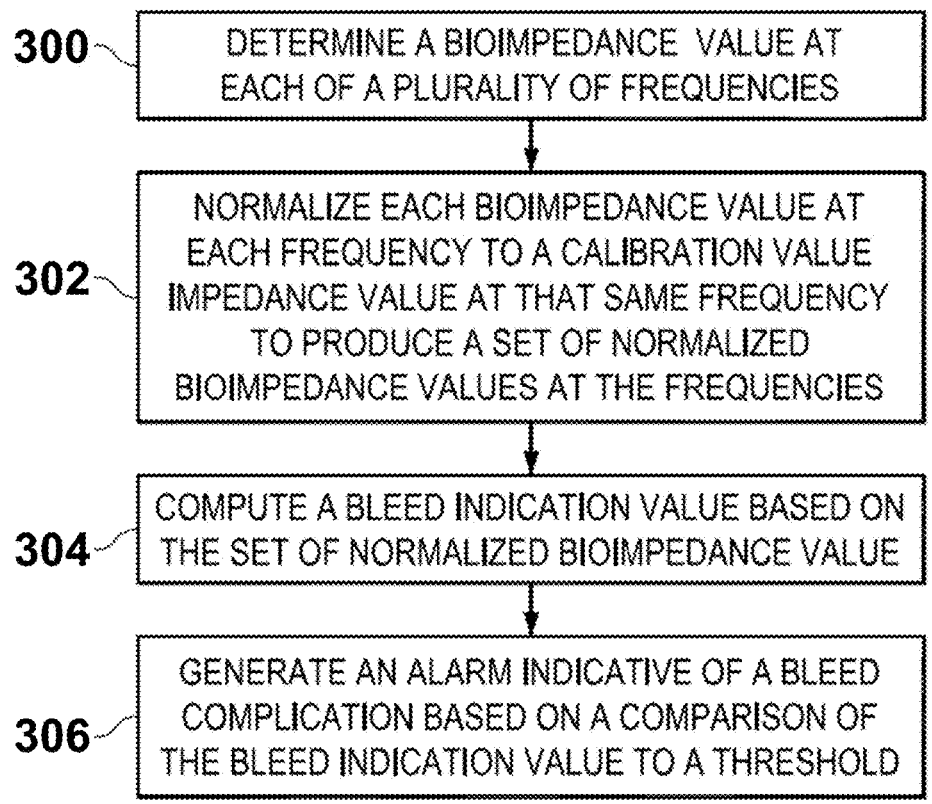

FIG. 12 shows a method for determining a bleed complication and generating an alarm based on whether a bleed complication is detected. The method of FIG. 12 may be performed by any of the apparatuses described herein (e.g., impedance assessment unit 100, external apparatus 135, etc.). The method includes a calibration phase performed preferably upon initial vascular access (e.g., before much if any blood could have accumulated outside the blood vessel even if an errant hole in the vessel was inadvertently created), and later during the catheterization procedure (at which time sufficient blood may have accumulated outside the vessel to be detected by the bioimpedance techniques described herein). The calibration phase of the method of FIG. 12 may be performed in addition to or in lieu of the calibration method of FIG. 11.

At 300, the method includes determining a bioimpedance value at each of a plurality of frequencies during the calibration phase. The frequencies may include any frequencies and any number of frequencies. In one example, the frequencies used to make the bioimpedance measurements include 5 KHz, 10 KHz, 50 KHz, 100 KHz, and 500 KHz. For purposes of illustration, five bioimpedance measurements are assumed and are designated as Z1, Z2, Z3, Z4, and Z5. The bioimpedance measurements Z1-Z5 taken during calibration are referred to herein as calibration bioimpedance values. The bioimpedance values measured during calibration may be normalized to themselves, that is, Z1/Z1, Z2/Z2, and so on. The normalized calibration bioimpedance values are referred to as "calibration ratios."

After calibration and periodically during the catheterization process (e.g., as specified by the user, by controller 150, or a processor in external apparatus 135), the method includes again making the bioimpedance measurements at the same frequencies. For purpose of illustration, the five such impedance values measured after calibration are referred to as ZA, ZB, ZC, ZD, and ZE. At 302, the method includes normalizing each bioimpedance value ZA-ZB at each frequency to a calibration bioimpedance value at that same frequency to produce a set of normalized bioimpedance values at the plurality of frequencies. In one example, the calibration bioimpedance value used to normalize each of the bioimpedance values ZA-ZE is the calibration bioimpedance values Z1-Z5 measured during calibration. More specifically, each bioimpedance value ZA-ZE is divided by itself (ZA/Z1, ZB/Z2, ZC/Z3, ZD/Z4, and ZE/Z5). If no bleed complication condition exists, then these ratios ought to be approximately 1. If a bleed condition exists following calibration, one or more of the ratios will diverge from 1.

The method includes determining whether the newly computed bioimpedance values over the various frequencies are significantly the same or different from the calibration bioimpedance values. The newly computed bioimpedance values being significantly different from the calibration bioimpedance values may indicate the occurrence of a bleed complication condition. The newly computed bioimpedance values not being significantly different from the calibration bioimpedance values may indicate that a bleed complication condition has not occurred.

At 304, the method includes computing a bleed indication value based on the set of normalized bioimpedance values. In one example, computing the bleed indication value includes computing, at each frequency, the absolute value of a difference between a calibration ratio (normalized calibration bioimpedance value) at that frequency and the subsequent normalized bioimpedance value at the same frequency. For example, the equation below illustrates this calculation for one frequency:

$$\left| \frac{Z1}{Z1} - \frac{ZA}{Z1} \right|$$

The bleed indication value further may be computed based on the sum of the absolute value computed above and the calibration ratio (normalized calibration bioimpedance value), and then averaging these values across all frequencies. The equation below illustrates an example of the aforementioned computation for one such frequency and is referred to as a bioimpedance rend value:

$$\frac{Z1}{Z1} + \left| \frac{Z1}{Z1} - \frac{ZA}{Z1} \right|$$

This calculation is performed as well for all frequencies and then the results are averaged to compute the bleed indication value.

The method may further include performing a statistical test on the set of normalized bioimpedance values acquired during calibration compared to the normalized bioimpedance values acquired subsequently. One example of such a test is the T-Test which produces a p-value (i.e., a confidence value). Inputs to the T-Test algorithm may include the average of the normalized calibration bioimpedance values, the average of the subsequently acquired normalized bioimpedance values (after calibration), and the number of elements being averaged (5 in the example above). A p-value less than 0.05 indicates that a difference in the averages is statistically significant, and a p-value greater than 0.05 indicates a lack of statistical significance of a difference in the averages.

The method includes (at 306) generating an alarm indicative of a bleed complication based on a comparison of the bleed indication value to a threshold. In one example, the threshold may be 1.4 and thus the average for the non-calibration normalized bioimpedance values being greater than 1.4 may indicate the occurrence of a bleed complication condition. This operation may also include the use of the p-value. For example, a bleed complication condition may be determined if both of the following conditions are true:

the average for the non-calibration normalized bioimpedance values is greater than 1.4 and the p-value is less than 0.05.

Further still, the apparatus may generate an alarm based on the above two conditions being true for at least two consecutive sets of bioimpedance values measured during the catheterization procedure.

During a catheterization procedure, the medical staff may want or need to replace an introducer sheath 12. For example, the doctor may want to switch out the existing catheter for a different catheter having a different diameter. As such, a different diameter sheath 12 may be needed. Because the sheaths 12 may be integral with the flush line 14 and impedance assessment unit 100, the entire introducer 10 may need to be replaced. However, the presently used introducer 10 and its impedance assessment unit 100 may have stored various impedance calibration values and impedance history for the patient up to that point (e.g., per the calibration and monitoring methods discussed above). Such data can be wirelessly transferred from the existing (old) introducer's impedance assessment unit 100 to a replacement (new) introducer impedance assessment.

Figure 13:
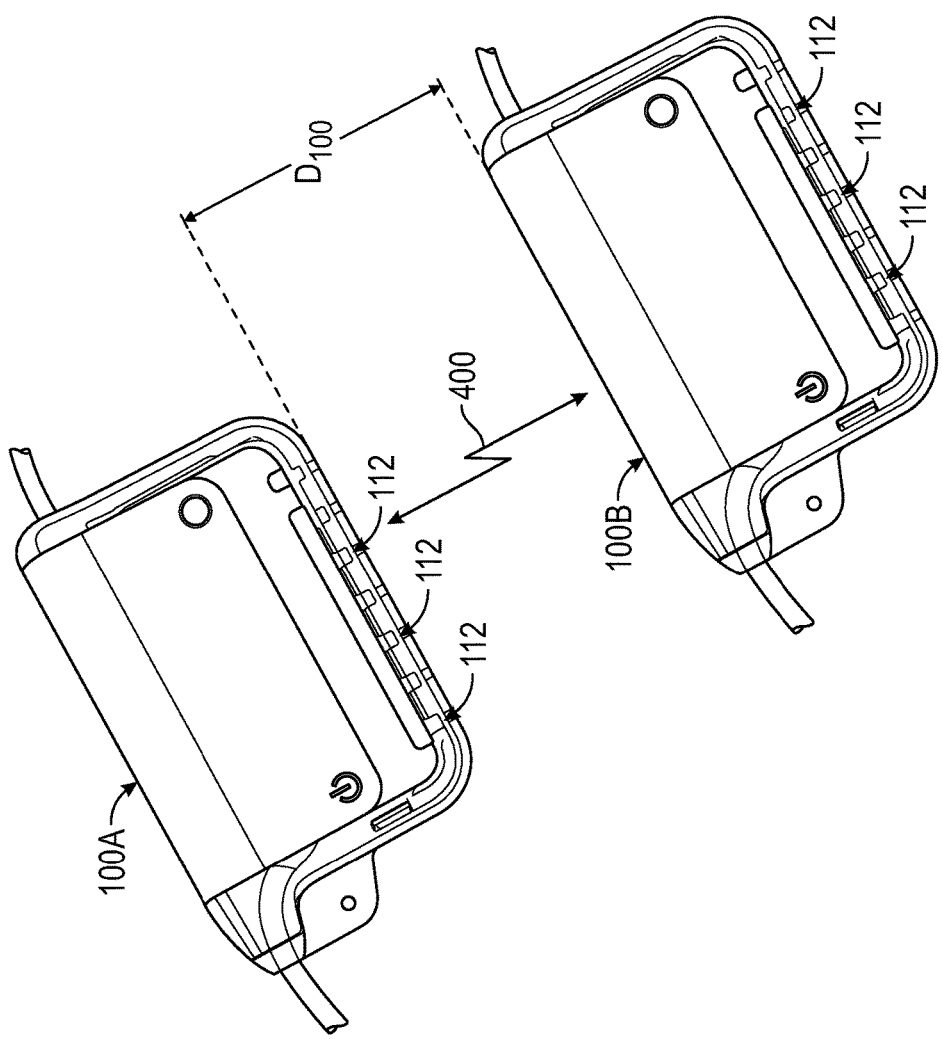
FIG. 13 is a perspective view of a pair of impedance assessment units transferring data through a wireless connection in accordance with the principles disclosed herein.

For example, referring now to FIG. 13, a first impedance assessment unit 100A and a second impedance assessment unit 100B are shown in close proximity to one another. In this embodiment, first unit 100A is coupled to an introducer (e.g., introducer 10) that is used first in time during a medical procedure as described above, and second unit 100B is coupled to a new or replacement introducer 10 that is to be used subsequent to the first introducer (and first unit 100A) during the procedure. In addition, it should be understood that both units 100A, 100B are coupled to the other components discussed above for two separate introducers (e.g., like introducer 10 shown in FIG. 1); however, only impedance assessment units 100A, 100B are shown in FIG. 13 for clarity and brevity.

During operations, once it is desirable to replace the introducer associated with first unit 100A, second unit 100B is brought into close enough proximity to allow a wireless connection 400 to form therebetween. Wireless connection 400 may be accomplished through any suitable wireless communication technology including, for example, NFC, BLUETOOTH®, WiFi (any of the IEEE 802.11x family of protocols), etc. In this embodiment, wireless connection 400 is formed between wireless transceivers (e.g., transceiver 152 shown in FIG. 9) within each unit 100A, 100B through NFC. As a result, connection 400 is formed between units 100A, 100B when they are disposed within a certain distance from one another. In FIG. 13, the distance between the units 100A and 100B (or between their wireless transceivers 152) is shown as $D_{100}$. In some embodiments, distance $D_{100}$ should be equal to or less than a threshold distance in order for a sufficient wireless connection 400 to form. The threshold distance, in some examples, is 10 cm. Wireless connection 400 may form either automatically or in response to a manual manipulation of unit 100A and/or unit 100B by a user. For example, in some embodiments, merely placing units 100A, 100B in close proximity to one another (e.g., within distance $D_{100}$) causes the connection 400 to form therebetween. As another example, in other embodiments, once units 100A, 100B are placed within the threshold distance from one another (or perhaps when units 100A, 100B are outside of the threshold distance when non NFC wireless technologies are utilized to form wireless connection 400), a user manually causes wireless connection 400 to form (e.g., by pushing a button on either unit 100A and/or unit 100B).

Upon establishing wireless connection 400, data, including, for example, prior calibration values, values of voltage, current, or impedance, and/or bleed detection data, is transferred from first unit 100A to second unit 100B via the wireless connection 400. The indicator lights 112 on either or both of the units 100A, 100B may illuminate to indicate a currently occurring data transfer. Once the data transfer between units 100A, 100B is completed, one or more of the indicator lights 112 on one or both of the units 100A, 100B light up to signal to the user that the data transfer is completed. The end of the data transfer may automatically cause the "old" unit 100A to transition to a standby mode (indicated by an indicator light 112 on the unit 100A). The new unit 100B transitions to an operating mode also as indicated by an indicator light 112 on the unit 100B. The indicator lights 112 thus indicate to the health care professional that the old unit 100A and its sheath 12 can be removed from the patient and the new unit 100B inserted in its place. At this point, the health care professional may replace the first introducer associated with impedance assessment unit 100A with the introducer associated with impedance assessment unit 100B, and the medical procedure may proceed with unit 100B measuring impedance values and detecting bleed complications either alone or in combination with an external apparatus (e.g., apparatus 135 in FIG. 10) in the manner previously described above.

Figure 14:
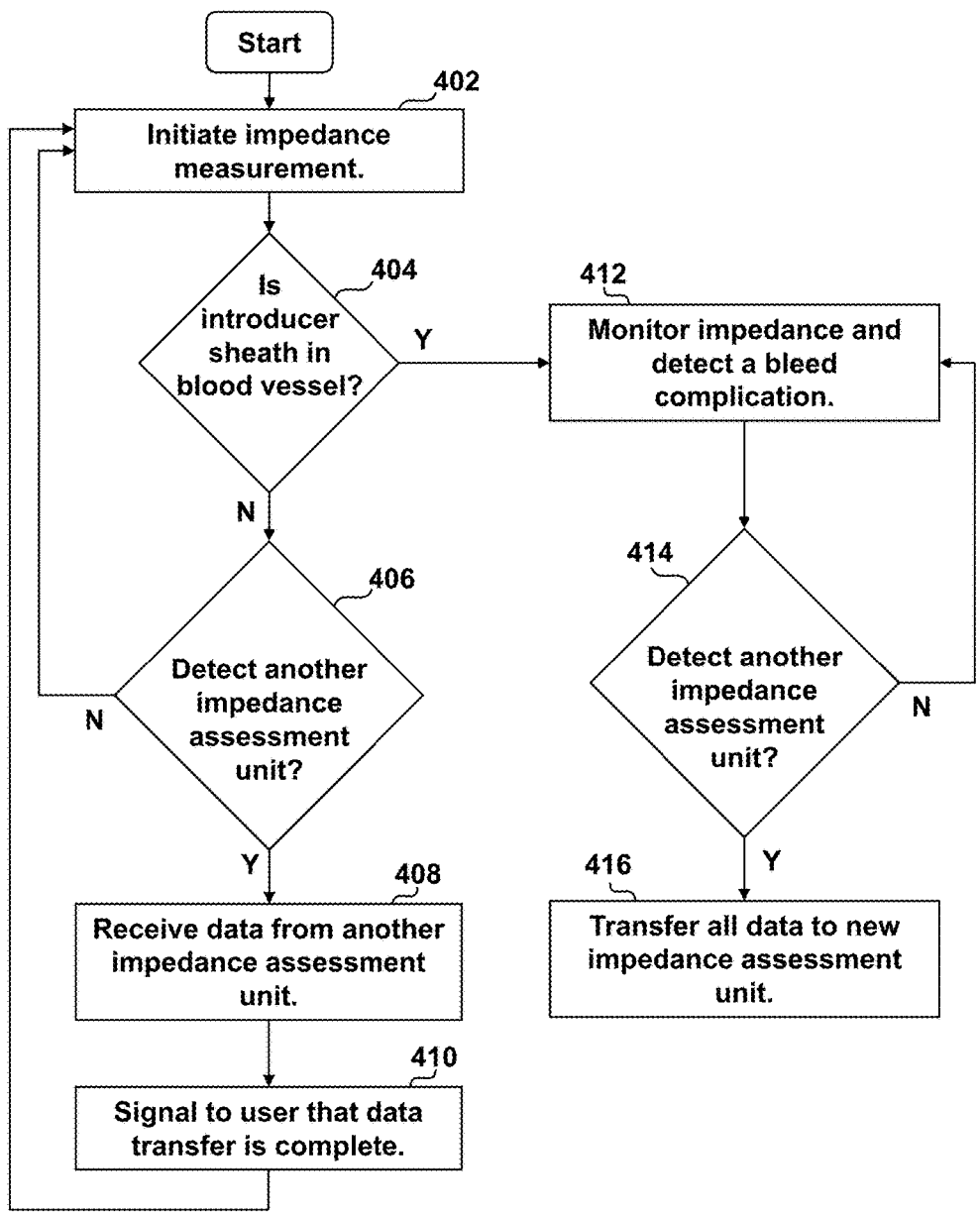
FIG. 14 is a block diagram of a operation logic for the impedance assessment unit of the introducer of FIG. 1.

Referring now to FIG. 14, a flow chart demonstrating an example of the operating logic of an impedance assessment unit (e.g., units 100, 100A, 100B) discussed herein is shown. For clarity, the features of the flow chart of FIG. 14 are discussed in light of an individual impedance assessment unit 100 such as that shown in FIG. 1 and described above; however, it should be appreciated that the features of flow chart of FIG. 14 may be applied and utilized along with any of the impedance assessment units discussed herein (e.g., impedance assessment units 100A, 100B). The operations depicted in the FIG. 14 can be performed in the order shown or in a different order. Further, two or more of the operations may be performed sequentially instead of serially.

Upon initially powering up an impedance assessment unit 100, an impedance measurement is initiated at 402 between any two of the electrodes 20a, 20b, 20c, 20d, previously described above. In some embodiments, an impedance measurement is initiated between one electrode (e.g., 20d) and each of the other electrodes (e.g., 20a, 20b, 20c), and in other embodiments, an impedance measurement is initiated between one of the electrodes 20a, 20b, 20c, 20d and an external electrode that is separate from introducer 10. A purpose of initiating the initial impedance measurement is to determine whether the introducer 10 newly powered on has been inserted into the patient. If it has, then impedance measurements should begin as part of the bleed detection process. If the introducer is not in the patient, then the device should await receiving wireless communications from another introducer currently in the patient to receive that device's calibration and other data as explained above.

As such, a decision is made at 404 as to whether the introducer sheath is in a blood vessel. This operation can be performed by attempting to measure an impedance value between the electrodes. If the measured impedance is above a threshold (indicative of an open circuit), a measured impedance value that is above the limit would indicate that the sheath's electrode(s) (and thus sheath 12) is outside the body of the patient. A measured impedance that is below the threshold indicates that the electrode(s) (and thus sheath 12) is inside the body of the patient. As a result, if the introducer sheath is determined not to be inside the patient (the "N"

branch) then the impedance assessment unit 100 enters into a standby or data acquisition mode during which operations 406-410 are performed. If, on the other hand, the introducer sheath is determined to be inside the patient (e.g., inside a blood vessel) (the "Y" branch from 404) then the impedance assessment unit 100 enters into a bleed detection mode at 412, during which impedance is measured to detect a bleed complication in the patient per any of the methods discussed above.

Once it is determined that the measured impedance in 402 is below the limit in 404 (the "YES" branch from 404), the impedance assessment unit attempts to detect at 406 another nearby impedance assessment units. The detection in 406 may be through a wireless connection (e.g., connection 400 previously described). Thus, in at least some embodiments, at 406 the impedance assessment unit 100 determines whether another impedance assessment unit (e.g., unit 100B) is within the predetermined distance and discussed above. If another impedance assessment unit is not detected at 406, a control loop routes back to 402 at which another impedance measurement is taken and assessed at 404 to determine again whether the impedance assessment unit is outside or inside the body of the patient. If, on the other hand, another impedance assessment unit is detected at 406, data is received from the other impedance assessment unit at 408. The data transfer at 408 may be the same as previously described above between impedance assessment units 100A, 100B shown in FIG. 13. Thereafter, once the data transfer at 408 is completed, the impedance assessment unit 100 is then directed at 410 to signal to the user in some fashion that the transfer has been completed. In some embodiments, the signaling at 410 is any one or more of an audible, vibratory, or visual indicator, or some combination thereof such as, for example, activation of one or more lights (e.g., indicator lights 112), an audible beep or tone, and/or a vibration of the impedance assessment unit 100. Once the data transfer is completed and the user is signaled at 408 and 410, respectively, another impedance measurement(s) is taken at 402 and evaluated at 404 to determine whether any one of the electrodes 20a, 20b, 20c, 20d (and thus sheath 12) is disposed within the body of the patient.

Returning now to the assessment of the initial impedance measurement at 404. As previously described, if it is determined that the impedance measurements taken in 402 is below the limit (which indicates that the sheath has been inserted into the patient), then normal impedance measurement and bleed detection operations per any of the methods described herein proceeds at 412. At some point during the monitoring at 412 (e.g., periodically such as once every 30 seconds), impedance assessment unit 100 again determines another impedance assessment unit is in wireless communication with it at 414. In some embodiments, the determination at 414 is made in the same manner described above in 406. If another impedance assessment unit is not detected at 414, bleed detection continues at 412. If, on the other hand, another impedance assessment unit is detected at 414, some or all data from the impedance assessment unit 100 is transferred to the detected impedance assessment unit at 416. The data transferred from the impedance assessment unit 100 at 416 may occur in the same manner as described above for units 100A, 1006 shown in FIG. 13.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A introducer, comprising:
   an introducer sheath for introducing a catheter into a blood vessel at an insertion point;
   a plurality of electrodes on the introducer sheath;
   a flush line coupled to the introducer sheath including a proximal end and a distal end; and
   an impedance assessment unit comprising:
     a body defining a cavity;
     a first port extending into the cavity; and
     a second port extending into the cavity;
   wherein the impedance assessment unit is coupled to the flush line between the proximal end and the distal end such that the flush line extends through the cavity between the first port and the second port; and
   wherein the impedance assessment unit is electrically coupled to the electrodes
   and is configured to inject a predetermined current or voltage into a first of the plurality of electrodes and measure a resulting voltage or current, respectively, from a second of the plurality of electrodes.

2. The introducer of claim 1, further comprising:
   a hub coupled to the introducer sheath;
   wherein the proximal end of the flush line is coupled to the hub.

3. The introducer of claim 1, further comprising a wireless communication unit coupled to the impedance assessment unit, wherein the impedance assessment unit is configured to communicate wirelessly with the wireless communication unit, and wherein the wireless communication unit is configured to communicate wirelessly with an external apparatus.

4. The introducer of claim 3, wherein the external apparatus comprises a computer or a bedside monitor.

5. The introducer of claim 1, wherein the impedance assessment unit is configured to detect a bleed condition at the insertion point by computing an impedance between the first electrode and the second electrode based on the predetermined current or voltage and the resulting voltage or current, respectively.

6. The introducer of claim 1, wherein the flush line includes a bent region in the cavity, wherein the bent region is configured to resist movement of the impedance assessment unit along the flush line between the proximal end and the distal end.

7. The introducer of claim 6, wherein the impedance assessment unit includes a power source aligned between the first port and the second port, and wherein the bent region extends around the power source.

8. The introducer of claim 1, further comprising:
   a plurality of conductors coupled to the impedance assessment unit;
   wherein at least one of the plurality of conductors is coupled to one of the plurality of electrodes;
   wherein the flush line includes a radially outermost surface and a throughbore; and wherein the plurality of conductors extend along the flush line, between the radially outermost surface and the throughbore.

9. The introducer of claim 8, wherein each of the plurality of electrodes is coupled to the impedance assessment unit through a respective one of the plurality of conductors.

10. An impedance assessment unit configured to be disposed on an introducer for inserting a catheter into a blood vessel at an insertion point, the impedance assessment unit comprising:
a body defining a cavity;
a first port extending into the cavity;
a second port extending into the cavity;
electronic components disposed within the cavity, wherein the electronic components are configured to inject a known current or voltage into a first of a plurality of electrodes coupled to an introducer sheath of the introducer and measure a resulting voltage or current, respectively, from a second of the plurality of electrodes;
a power source disposed within the cavity;
wherein the cavity, the first port, and the second port are configured to receive a flush line of the introducer therethrough; and
wherein the electronic components and the power source are arranged within the cavity such that when the flush line is received through the first port, the second port, and the cavity, the flush line includes a bent region extending around the power source, wherein the bent region is configured to resist movement of the impedance assessment unit along the flush line.

11. The impedance assessment unit of claim 10, further comprising a wireless transceiver coupled to the electronic components, wherein the wireless transceiver is configured to communicate with a wireless communication unit.

12. The impedance assessment unit of claim 11, wherein the wireless transceiver is configured to communicate with the wireless communication unit through near field communications.

13. The impedance assessment unit of claim 10, wherein the impedance assessment unit is configured to detect a bleed condition at the insertion point by computing an impedance between the first electrode and the second electrode based on the known current or voltage and the resulting voltage or current, respectively.

14. A introducer, comprising:
an introducer sheath for introducing a catheter into a blood vessel at an insertion point;
a plurality of electrodes on the introducer sheath;
a hub coupled to the introducer sheath;
a flush line including a proximal end coupled to the hub, a distal end, a radially outermost surface extending between the proximal end and the distal end, and a throughbore also extending between the proximal end and the distal end;
an impedance assessment unit coupled to the flush line between the proximal end and the distal end, wherein the impedance assessment unit includes:
a body defining a cavity;
a first port extending into the cavity; and
a second port extending into the cavity;
wherein the impedance assessment unit is coupled to the flush line such that the flush line extends through the cavity between the first port and the second port; and
a plurality of conductors extending along the flush line, between the radially outermost surface and the throughbore, and coupled to the impedance assessment unit, wherein at least one of the plurality of conductors is also coupled to a first of the plurality of electrodes and at least another one of the plurality of conductors is also coupled to a second of the plurality of electrodes;
wherein the impedance assessment unit is configured to inject a known current or voltage into the first electrode and measure a resulting voltage or current, respectively, from the second electrode.

15. The introducer of claim 14, further comprising a wireless communication unit coupled to the impedance assessment unit, wherein the impedance assessment unit is configured to communicate wirelessly with the wireless communication unit, and wherein the wireless communication unit is configured to communicate wirelessly with an external apparatus.

16. The introducer of claim 15, wherein the impedance assessment unit is configured to communicate with the wireless communication unit through near field communication.

17. The introducer of claim 14, wherein the impedance assessment unit is configured to detect a bleed condition at the insertion point by computing an impedance between the first electrode and the second electrode based on the known current or voltage and the resulting voltage or current, respectively.

\* \* \* \* \*